US010352694B2

(12) United States Patent
Chen et al.

(10) Patent No.: US 10,352,694 B2
(45) Date of Patent: Jul. 16, 2019

(54) CONTACTLESS DUAL-PLANE POSITIONING METHOD AND DEVICE

(71) Applicant: INDUSTRIAL TECHNOLOGY RESEARCH INSTITUTE, Hsinchu (TW)

(72) Inventors: Guo-Dung Chen, New Taipei (TW); Bo-Ching He, Hsinchu (TW); Wei-En Fu, Taoyuan (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 226 days.

(21) Appl. No.: 15/652,212

(22) Filed: Jul. 17, 2017

(65) Prior Publication Data

US 2018/0299266 A1 Oct. 18, 2018

(30) Foreign Application Priority Data

Apr. 18, 2017 (TW) .............................. 106112989 A

(51) Int. Cl.
*G01B 15/00* (2006.01)
*G01N 23/02* (2006.01)
*G03F 7/20* (2006.01)

(52) U.S. Cl.
CPC ............. *G01B 15/00* (2013.01); *G01N 23/02* (2013.01); *G03F 7/70616* (2013.01); *G03F 7/70625* (2013.01)

(58) Field of Classification Search
CPC ...... G01B 15/00; G01N 23/02; G01N 23/207; G01N 17/004; G03F 7/70616;
(Continued)

(56) References Cited

U.S. PATENT DOCUMENTS 4,848,911 A  7/1989 Uchida et al.
5,133,599 A  7/1992 Sommargren
(Continued)

FOREIGN PATENT DOCUMENTS

CN  104807841 A  7/2015
EP  2 863 213 A1  4/2015
(Continued)

OTHER PUBLICATIONS

Notice of Allowance dated May 9, 2018 in Taiwanese application No. 106112989.
(Continued)

*Primary Examiner* — David P Porta
*Assistant Examiner* — Fani Boosalis
(74) *Attorney, Agent, or Firm* — Maschoff Brennan

(57) ABSTRACT

A contactless dual-plane positioning method is disclosed. In this method, an X ray is provided. The X ray passes through a first test piece along a light incident axis. A scattering pattern generated by the X ray passing through the first test piece, and a scatting light intensity corresponding to the scattering pattern are obtained. According to the scattering light intensity, the first test piece is pivoted along a first axis or a second axis until the scattering intensity is greater than or equal to a predetermined intensity. At least three measurement distances between a second test piece and the first test piece are then obtained. According to the measurement distances, an included angle between the second test piece and the light incident axis is adjusted by pivoting the second test piece along a third axis or a fourth axis until the differences between any two measurement distances are less than a predetermined threshold value.

12 Claims, 12 Drawing Sheets

(58) Field of Classification Search
CPC ...... G03F 7/70625; G03F 7/00; G03F 7/0037; G03F 7/70725; G03F 7/70733; G03F 7/70833; G03F 7/70716; G03F 7/70608
See application file for complete search history.

(56) References Cited

U.S. PATENT DOCUMENTS

| | | | |
|---|---|---|---|
| 5,532,815 | A | 7/1996 | Kipman et al. |
| 6,885,459 | B2 | 4/2005 | Müller |
| 7,062,010 | B2 | 6/2006 | Matsumoto |
| 7,298,496 | B2 | 11/2007 | Hill |
| 7,433,048 | B2 | 10/2008 | Park |
| 7,483,120 | B2 * | 1/2009 | Luttikhuis ............. G03B 27/53 355/53 |
| 8,390,820 | B2 | 3/2013 | Klaver et al. |
| 8,834,146 | B2 | 9/2014 | Saha et al. |
| 8,937,707 | B2 | 1/2015 | Jansen et al. |
| 9,377,698 | B2 | 6/2016 | Shibazaki |
| 9,576,825 | B2 | 2/2017 | Figura |
| 2005/0286042 | A1 * | 12/2005 | Schoormans ......... G03F 9/7011 355/77 |
| 2008/0273662 | A1 | 11/2008 | Yun et al. |
| 2012/0057677 | A1 | 3/2012 | Vogtmeier et al. |
| 2014/0270060 | A1 | 9/2014 | Date et al. |
| 2015/0260663 | A1 | 9/2015 | Yun et al. |
| 2015/0300965 | A1 | 10/2015 | Sezginer et al. |
| 2015/0355554 | A1 | 12/2015 | Mathijssen |
| 2016/0061590 | A1 | 3/2016 | Pandey |

FOREIGN PATENT DOCUMENTS

| | | |
|---|---|---|
| JP | 2003-7601 A | 1/2003 |
| JP | 4583759 B2 | 11/2010 |
| JP | 5650328 B2 | 1/2015 |
| TW | 212829 B | 9/1993 |
| TW | 200538704 A | 12/2005 |
| TW | I269865 B | 1/2007 |
| TW | I328720 B | 8/2010 |
| TW | I344060 B | 6/2011 |
| TW | I414756 B | 11/2013 |
| TW | I467348 B | 1/2015 |
| TW | 201515517 A | 4/2015 |
| TW | I499760 B | 9/2015 |
| TW | I515518 B | 1/2016 |
| TW | 201614188 A | 4/2016 |
| TW | 201620070 A | 6/2016 |
| TW | I553770 B | 10/2016 |
| WO | 03/064977 A2 | 8/2003 |
| WO | 2012/028166 A1 | 3/2012 |

OTHER PUBLICATIONS

Ho et al., "A Laboratory Scale Critical-Dimension Small-Angle X-ray Scattering Instrument", American Institute of Physics, AIP Conference Proceedings, vol. 931, Issue 1, 2007, pp. 382-386.

Hu et al., "Small angle x-ray scattering metrology for sidewall angle and cross section of nanometer scale line gratings", Journal of Applied Physics, vol. 96, Issue 4, Aug. 15, 2004, pp. 1983-1987.

Jones et al., "Small angle x-ray scattering for sub-100 nm pattern characterization", Applied Physics Letters, vol. 83, Issue 19, Nov. 10, 2003, pp. 4059-4061.

Wang et al., "CD-SAXS Measurements Using Laboratory-Based and Synchrotron-Based Instruments", Proceedings of SPIE—The International Society for Optical Engineering, vol. 6922, 2008, pp. 69222E-1-69222E-7.

* cited by examiner

CONTACTLESS DUAL-PLANE POSITIONING METHOD AND DEVICE

CROSS REFERENCE TO RELATED APPLICATION

This application claims the priority benefit of Taiwan application serial no. 106112989, filed on Apr. 18, 2017. The entirety of the above-mentioned patent application is hereby incorporated by reference herein.

TECHNICAL FIELD

The technical field generally relates to a contactless dual-plane positioning method and a contactless dual-plane positioning device.

BACKGROUND

The line width for semiconductor manufacturing is getting smaller and smaller. The difficulty for element inspection is accordingly increased while the critical dimension (CD) of the manufacturing process is decreasing. Therefore, the semiconductor industry needs an inspection technology with features of high-resolution capability, nondestructive-inspection and high efficiency to fulfill the inspection requirements of the semiconductor manufacturing process. According to current trends, a transmission small angle X-ray scattering (tSAXS) would be an important inspection technology for the next generation.

However, the duration of the measurement is too long for current commercial use of tSAXS devices or laboratory use of tSAXS devices, which are not qualified for efficiency requirements of the production line detection. Therefore, in an inspection method, the process duration of the measurement and the analysis of the process critical dimension could be shortened by developing a scattering enhancement module to directly enhance the scattering intensity of the X ray scattering. By doing so, the inspection efficiency of the critical dimension of the manufacturing process for the tSAXS devices could be significantly improved.

However, in this inspection method, an enhancing piece is disposed in front of a test piece. In addition to that the enhancing piece is controlled to be parallel to the test piece; a range of the distance between these two pieces requires to be further controlled to tens up to hundreds of nanometers to achieve an enhanced result. Currently, there is no feasible way to adjust these two pieces to be at appropriate positions under such small scale conditions. Therefore, how to adjust the enhancing piece and the test piece to be at appropriate relative positions is an important issue so far.

SUMMARY OF THE DISCLOSURE

A contactless dual-plane positioning method and a contactless dual-plane positioning device are provided according to embodiments of this disclosure. A test piece and an enhancing piece may be disposed accurately enough at predetermined relative positions, so as to raise the efficiency for production line detection.

According to an embodiment of this disclosure, the contactless dual-plane positioning method comprises the following steps. An X ray is provided, wherein the X ray passes through a first test piece along a light incident axis. A scattering pattern generated by the X ray passing through the first test piece, and a scattering light intensity corresponding to the scattering pattern are obtained. According to the scattering light intensity, the first test piece is pivoted along a first axis or a second axis until the scattering intensity is greater than or equal to a predetermined intensity. At least three measurement distances between a second test piece and the first test piece are then obtained. According to the three measurement distances, an included angle between the second test piece and the light incident axis is adjusted by pivoting the second test piece along a third axis or a fourth axis until the differences between any two of the three measurement distances are less than a predetermined threshold value.

According to another embodiment of this disclosure, the contactless dual-plane positioning device includes a light source, a first multi-axis moving platform, a second multi-axis moving platform, a sensing module, three shift measurement sensors and a controlling module. The controlling module is electrically connected to the sensing module, the first multi-axis moving platform, the second multi-axis moving platform and the three shift measurement sensors. The light source has a light emitting end. The light source provides an X ray through the light emitting end, wherein the X ray propagates along a light incident axis. The first multi-axis moving platform moves or pivots a first test piece along multiple axes. The second multi-axis moving platform moves or pivots a second test piece along multiple axes. The sensing module has a light sensing plane, wherein the light sensing plane faces the light emitting end. The first multi-axis moving platform and the second multi-axis moving platform are disposed between the light emitting end and the light sensing plane, wherein the sensing module obtains a scatting pattern generated by the X ray passing through the first test piece. The three shift measurement detectors obtain at least three measurement distances between the first test piece and the second test piece. The three measurement detectors are not collinear. The light incident axis passes through a plane defined by these three shift measurement detectors. The controlling module obtains a scattering light intensity corresponding to the scatting pattern and to drives the first multi-axis moving platform which pivots the first test piece along a first axis or a second axis according to the scattering light intensity until the scatting light intensity is greater than a predetermined intensity. The controlling module drives the second multi-axis moving platform which pivots the second test piece along a third axis or a fourth axis according to the three measurement distances until differences of any two of the three measurement distances are less than a predetermined threshold value. The first axis is different from the second axis. The first axis, the second axis and the light incident axis are non-coplanar.

The foregoing will become better understood from a careful reading of a detailed description provided herein below with appropriate reference to the accompanying drawings

DETAILED DESCRIPTION OF DISCLOSED EMBODIMENTS

Figure 1:
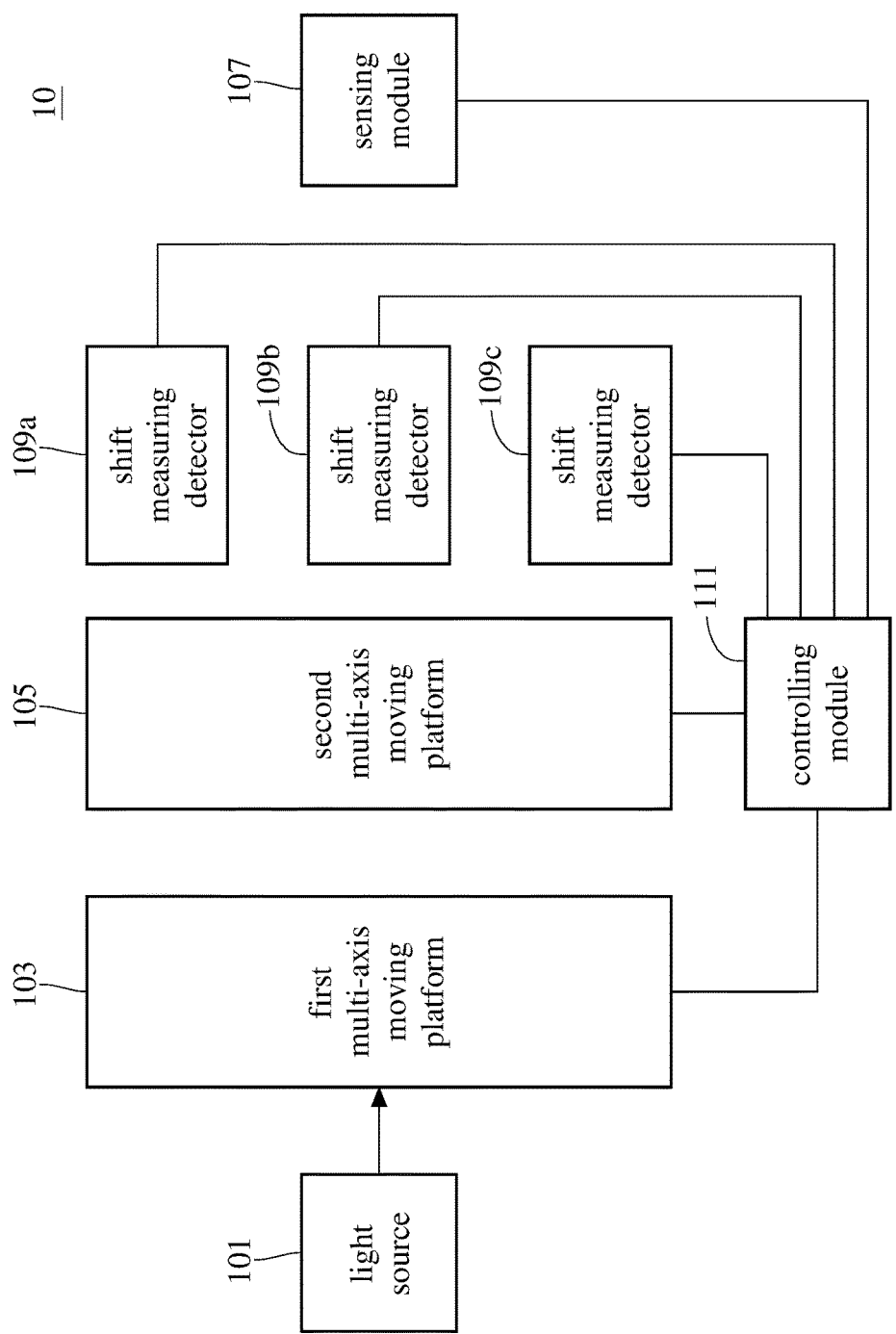
FIG. 1 is a block diagram illustrating a contactless dual-plane positioning device according to an embodiment of the disclosure.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

Figure 2:
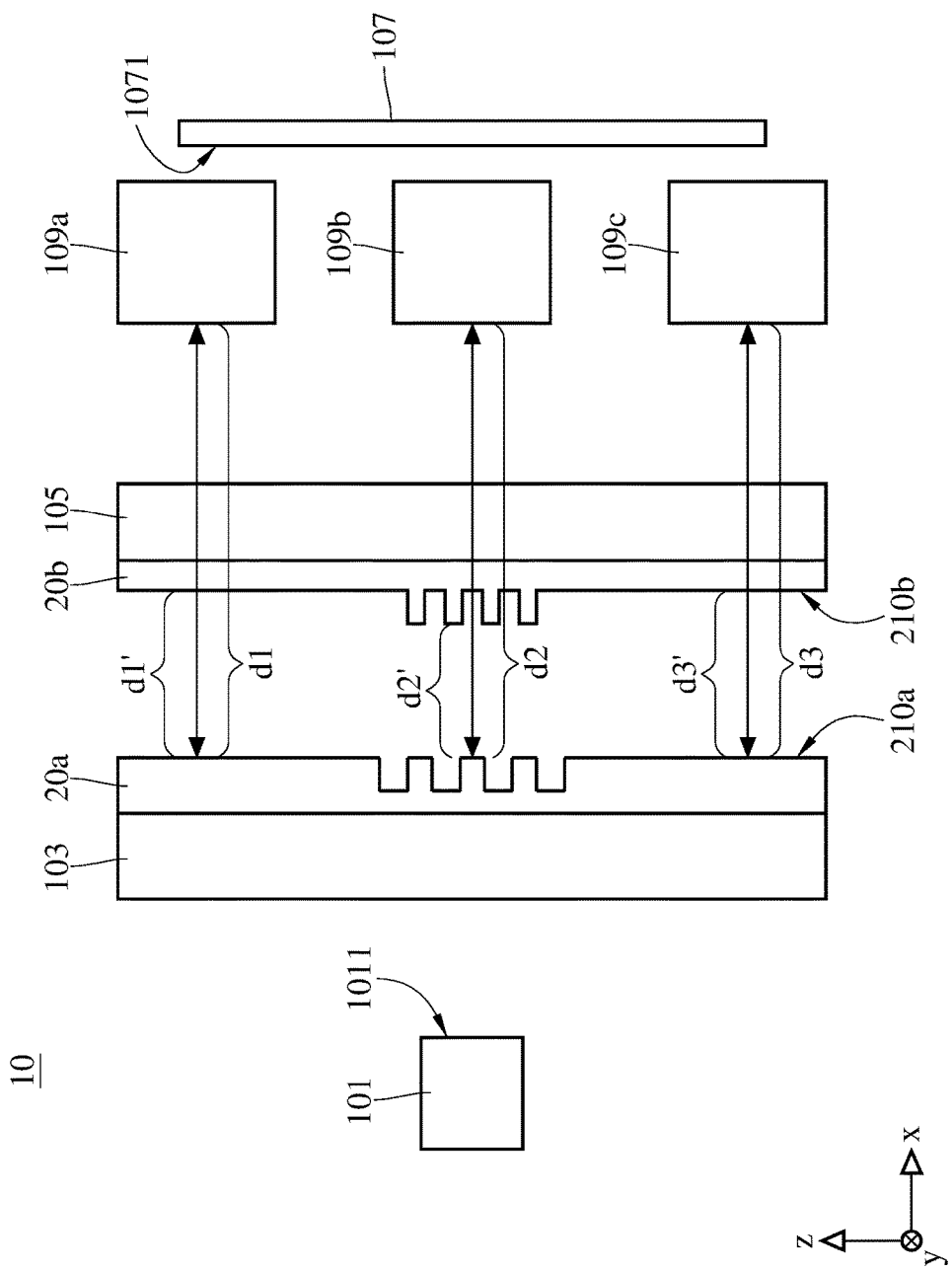
FIG. 2 is a schematic diagram illustrating the architecture of the contactless dual-plane positioning device of FIG. 1, according to an embodiment of the disclosure.

Please refer to FIG. 1 and FIG. 2, wherein FIG. 1 shows a block diagram illustrating a contactless dual-plane positioning device 10 according to an embodiment of this disclosure, and FIG. 2 shows a schematic diagram of the architecture of the a contactless dual-plane positioning device 10 according to an embodiment of this disclosure. As shown in FIG. 1, the contactless dual-plane positioning device 10 includes a light source 101, a first multi-axis moving platform 103, a second multi-axis moving platform 105, a sensing module 107, three shift measuring detectors 109a, 109b, and 109c, and a controlling module 111. The controlling module 111 is electrically connected to the first multi-axis moving platform 103, the second multi-axis moving platform 105, the sensing module 107, and the three shift measuring detectors 109a, 109b, and 109c. As shown in FIG. 2, the first multi-axis moving platform 103 and the second multi-axis moving platform 105 are disposed between the light source 101 and the sensing module 107. As shown in FIG. 2, the first multi-axis moving platform 103 is disposed between the light source 101 and the second multi-axis moving platform 105. The second multi-axis moving platform 105 is disposed between the first multi-axis moving platform 103 and the sensing module 107.

The light source 101 has a light emitting end 1011. The light source 101 provides an X ray through the light emitting end 1011, wherein the X ray propagates along a light incident axis. In order to explain more clearly, an X axis, a Y axis and a Z axis are used in FIG. 2. In this embodiment, the light incident axis is parallel to the X axis.

The first multi-axis moving platform 103 moves or pivots a first test piece 20a along multiple axes. The second multi-axis moving platform 105 moves or pivots a second test piece 20b along multiple axes. The first test piece 20a and the second test piece 20b are adhered to or clamped by the first multi-axis moving platform 103 and the second multi-axis moving platform 105, respectively. The first test piece 20a includes a periodic structure. The periodic structure is disposed on a first periodic structural surface 210a. The second test piece 20b includes a periodic structure. The periodic structure is disposed on a second periodic structural surface 210b. The first periodic structural surface 210a faces the second periodic structural surface 210b. The periodic structures of the first test piece 20a and the second test piece 20b may be the same or different.

According to another embodiment, the first test piece 20a and the second test piece 20b may be regarded as two different gratings. In an embodiment, the first test piece 20a may be one of a test piece and an enhancing piece. The second test piece 20b may be the other one of the test piece and the enhancing piece. The test piece may be, for example, a complete structure or a partial structure of a wafer to be tested. The enhancing piece-may be, for example, a grating with a designed structure. When the X ray passes through the test piece or the enhancing piece, a scattering pattern is formed by the scattering of the X ray due to the structures of the test piece. There is higher scattering intensity in a partial area of the scattering pattern. A person having ordinary skill in the art may design the structures of the test piece and the enhancing piece according to practical needs.

Figure 3A:
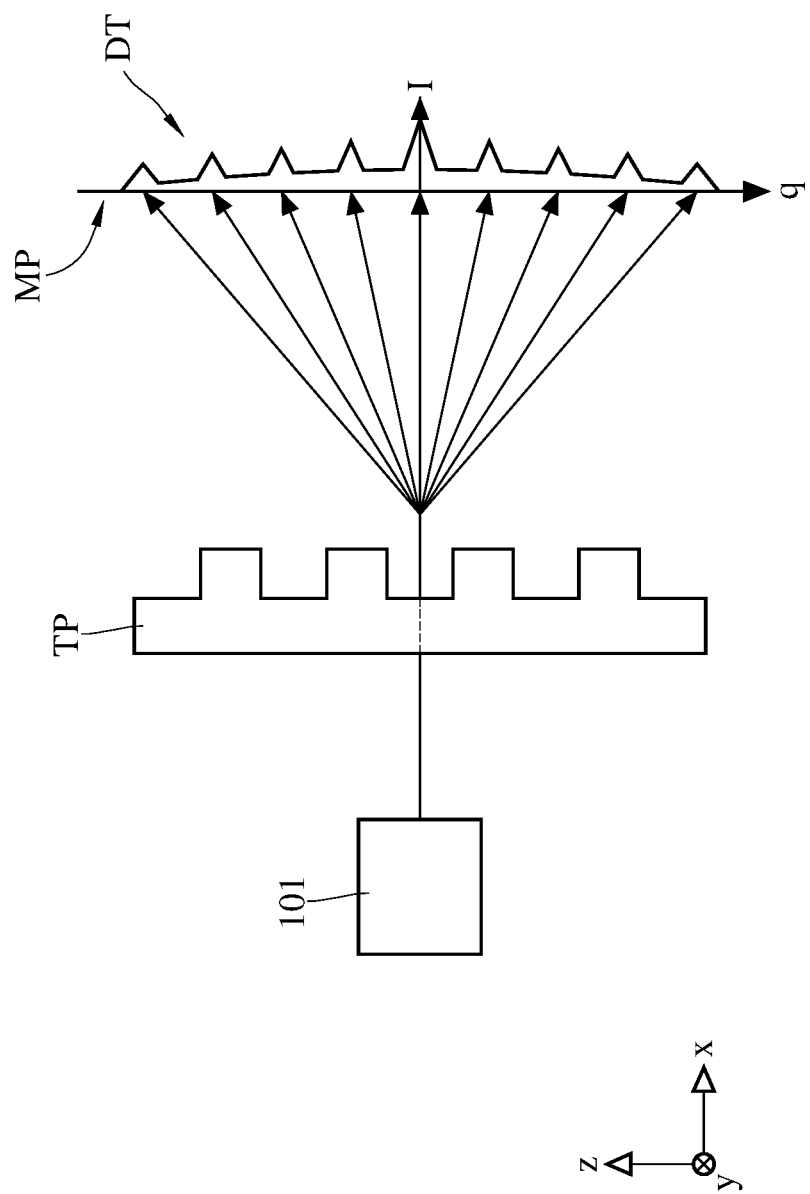
FIG. 3A is a schematic view showing an intensity distribution of a scattering pattern formed by the X ray passing through the test piece, according to an embodiment of the disclosure.
Figure 3B:
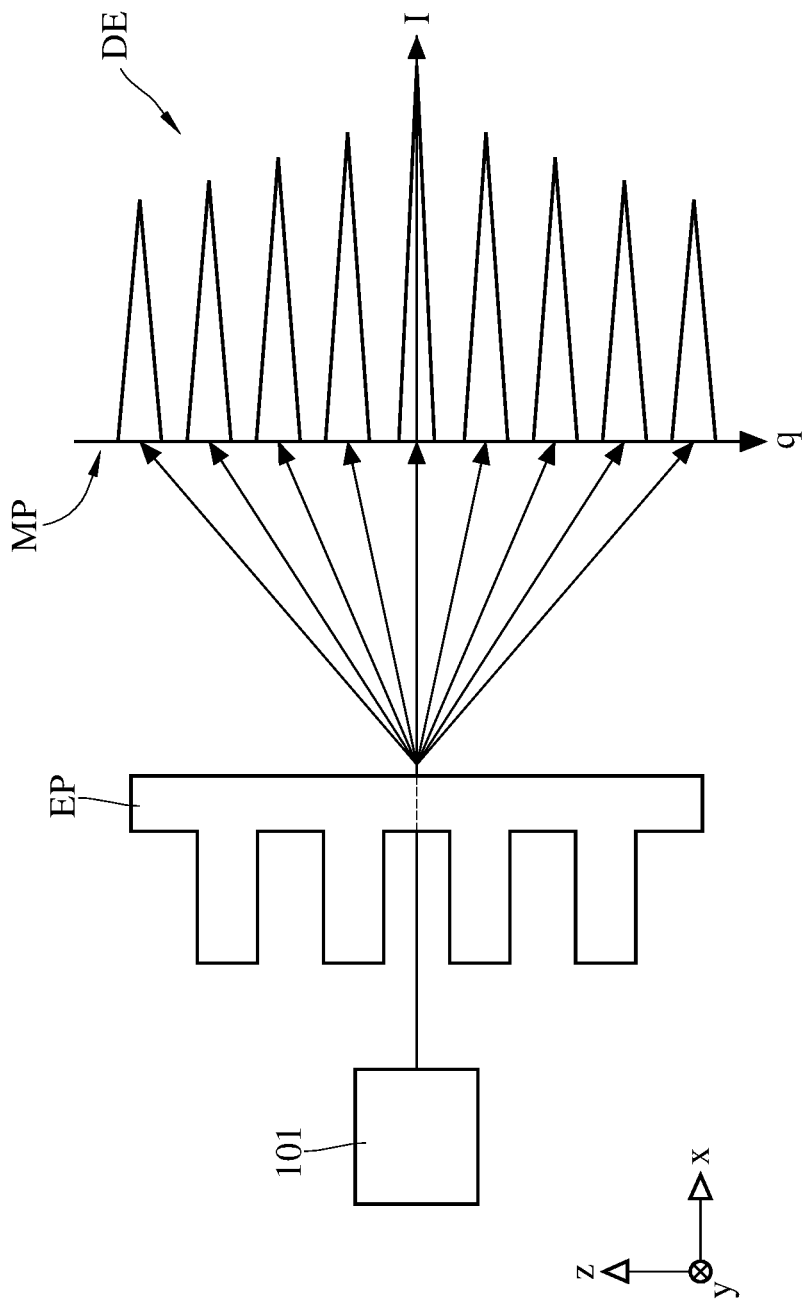
FIG. 3B is a schematic view showing an intensity distribution of a scattering pattern formed by the X ray passing through the enhancing piece, according to an embodiment of the disclosure.
Figure 3C:
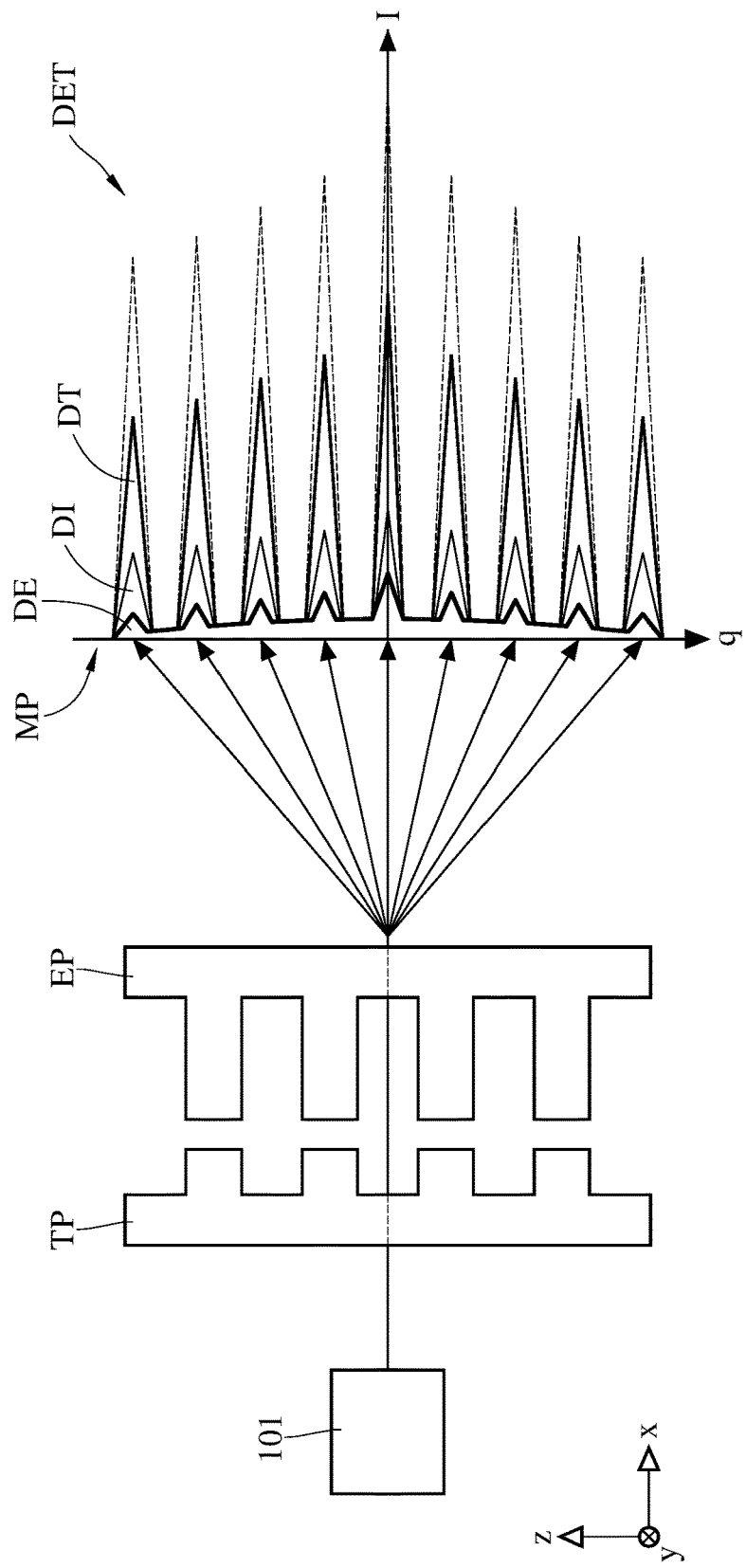
FIG. 3C is a schematic view showing an intensity distribution of an enhanced scattering pattern formed by the X ray passing through the test piece and the enhancing piece, according to an embodiment of the disclosure.

In practice, the shape of the scattering pattern is based on the type of the light source 101 and the structures of the first test piece 20a and the second test piece 20b. The scattering pattern formed by the X ray passing through the test piece is different from the scattering pattern formed by the X ray passing through the enhancing piece. Referring to FIG. 3A, FIG. 3B, and FIG. 3C, wherein FIG. 3A is a schematic view showing an intensity distribution of a scattering pattern formed by the X ray passing through the test piece, according to an embodiment of the disclosure, FIG. 3B is a schematic view showing an intensity distribution of a scattering pattern formed by the X ray passing through the enhancing piece, according to an embodiment of the disclosure, and FIG. 3C is a schematic view showing an intensity distribution of an enhanced scattering pattern formed by the X ray passing through the test piece and the enhancing piece, according to an embodiment of the disclosure.

In more details, FIG. 3A shows a scenario in which the X ray passes through the test piece TP and an intensity distribution DT of the scattering pattern formed by the X ray. To be more clearly, the corresponding scattering pattern formed on a measuring plane MP by the X ray passing through the test piece TP is a plane pattern. Different areas of the plane pattern have different scattering intensities according to the scattering conditions of the X ray. FIG. 3A shows a schematic view of the intensity distribution DT on a certain reference line of the plane pattern, wherein a q axis corresponding to the intensity distribution DT represents a wave-vector variation of the X ray before scattering and after scattering. An I axis corresponding to an intensity distribution D1 represents the scattering intensity. The definition of the axes of the scattering pattern may be modified according to actual needs of a person having ordinary skill in the art after reading this disclosure. Similarly, FIG. 3B shows a scenario in which the X ray passes through an enhancing piece EP and an intensity distribution DE of an enhanced scattering pattern. As shown in FIG. 3C, when the distance between the test piece TP and the enhancing piece EP is less than an interference distance, an interference phenomenon occurs while the X ray passes through the test piece TP and the enhancing piece EP. Therefore, the intensity distribution shown in FIG. 3C is the superimposed result of the intensity distribution DT shown in FIG. 3A, the intensity distribution DE shown in FIG. 3B and the interference component DI. The interference distance is related to, but not limited to the wavelength of the light source, the structure of the test piece and the structure of the enhancing piece EP. In an embodiment the interference distance is, for example, 500 nm.

Referring to FIG. 2 again, the sensing module 107 includes a light sensing plane 1071. The light sensing plane 1071 faces the light emitting end 1011. The light sensing plane 1071 is used as the aforementioned measuring plane MP. The sensing module 107 obtains the scattering pattern formed by the X ray passing through the first test piece 20a and the second test piece 20b. In practice, the controlling module 111 may drive the second multi-axis moving platform 105 to move the second test piece 20b along the Y axis or the Z axis away from the light incident axis (that is, the X axis). The sensing module 107 may then obtain the scattering pattern formed by the X ray passing through the first test piece 20a only. On the other hand, the first multi-axis moving platform 103 and the second multi-axis moving platform 105 are driven to move the first test piece 20a and the second test piece 20b to an appropriate relative position on the light incident axis. The sensing module 107 may then obtain the scattering pattern, which is formed by the X ray passing the first test piece 20a and the second test piece 20b, through the light sensing plane 1071. In practice, the first multi-axis moving platform 103 and the second multi-axis moving platform 105 may have, but not limited to, a skeleton structure or a light guide structure for providing a propagation path for the X ray passing through the first multi-axis moving platform 103 and the second multi-axis moving platform 105.

The sensing module 107 may be disposed on the second multi-axis moving platform 105 or disposed independently. A person having ordinary skill in the art may determine the positions of the sensing module 107 and the light sensing plane 1071 according to the platform structure sizes or the optical characteristics of the first multi-axis moving platform 103, the second multi-axis moving platform 105, the first test piece 20a and the second test piece 20b.

The shift measuring detectors 109a, 109b, and 109c respectively obtain at least three measurement distances d1', d2' and d3' between the first test piece 20a and the second test piece 20b. The shift measuring detectors 109a, 109b, and 109c are not collinear. The shift measuring detectors 109a, 109b, and 109c form a plane. In other words, the light incident axis passes through the plane defined by the shift measuring detectors 109a, 109b, and 109c. The positions of the shift measuring detectors 109a, 109b, and 109c are not limited to the points displayed on the Figures. As long as that positions used for shift measuring detectors 109a, 109b, and 109c will not interfere the propagation of the X ray and may obtain the measurement distances d1', d2' and d3'. The shift measuring detectors 109a, 109b, and 109c may be contactless measuring detectors, the measuring methods of the shift measuring detectors 109a, 109b, and 109c will not be limited herein.

According to an embodiment of this disclosure, the shift measuring detectors 109a, 109b, and 109c are disposed on the second multi-axis moving platform 105. The platform structure sizes of the second multi-axis moving platform 105 have already been known. Using a partial structure of the second multi-axis moving platform 105 as a reference point, the shift measuring detectors 109a, 109b, and 109c may directly measure the at least three measurement distances d1', d2' and d3' between the first test piece 20a and the second test piece 20b. Under the situation that platform structure sizes of the second multi-axis moving platform 105 have already been known, the relative positions of the shift measuring detectors 109a, 109b, and 109c are not limited. In other words, the shift measuring detectors 109a, 109b, and 109c are coplanar or non-coplanar. According to an embodiment, the shift measuring detectors 109a, 109b, and 109c respectively measure the distances d1, d2 and d3 that the shift measuring detectors 109a, 109b, and 109c relate to and the first test piece 20a. A back end (for example, the controlling module 111) converts the distances d1, d2 and d3 to the measurement distances d1', d2' and d3' according to the platform structure sizes of the second multi-axis moving platform 105. According to another embodiment, since the shift measuring detectors 109a, 109b, and 109c and the second test piece 20b are coplanar, therefore, the measuring results of the shift measuring detectors 109a, 109b, and 109c are measurement distances d1', d2' and d3'.

According to another embodiment, the shift measuring detectors 109a, 109b, and 109c are disposed independently outside the second multi-axis moving platform 105. When both the distances between the shift measuring detectors 109a, 109b, and 109c and the second multi-axis moving platform 105, and the platform structure sizes of the second multi-axis moving platform 105 have already been known, a back end (for example, the controlling module 111 or a server) may measure the distances d1, d2 and d3 that the shift measuring detectors 109a, 109b, and 109c, relate to the first test piece 20a, then may further convert the distances d1, d2 and d3 to the three measurement distances d1', d2' and d3' between the first test piece 20a and the second test piece 20b. In the embodiment, the measurement distances d1', d2' and d3' are obtained by the shift measuring detectors 109a, 109b, and 109c. However, the measuring method used for measurement distances is not limited to the aforesaid embodiment. A person having ordinary skill in the art may arrange the quantity and the relative positions of the shift measuring detectors according to actual needs.

The controlling module 111 obtains the scattering light intensity corresponding to the scattering pattern, and accordingly, drives the first multi-axis moving platform 103 to pivot the first test piece 20a along a first axis or a second axis until the scattering light intensity is greater than a predetermined intensity. The first axis is different from the second axis. Also, the first axis and the second axis are non-coplanar. In order to explain clearly, the first axis is defined as the Y axis while the second axis is defined as the Z axis (that is, any two of the first axis, the second axis and the light incident axis are orthogonal).

Figure 4A:
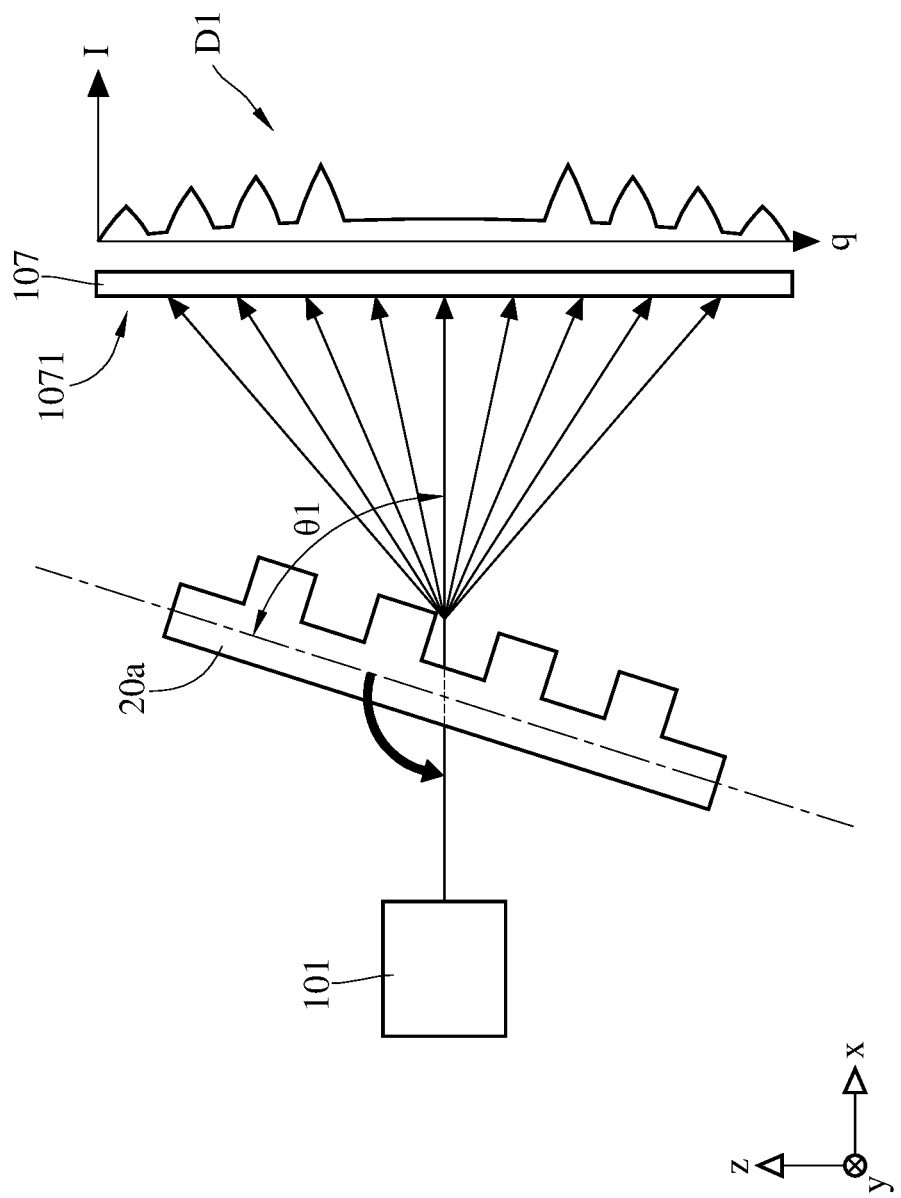
FIG. 4A is a schematic view showing an intensity distribution for that the first test piece is not orthogonal to X axis according to an embodiment of this disclosure.
Figure 4B:
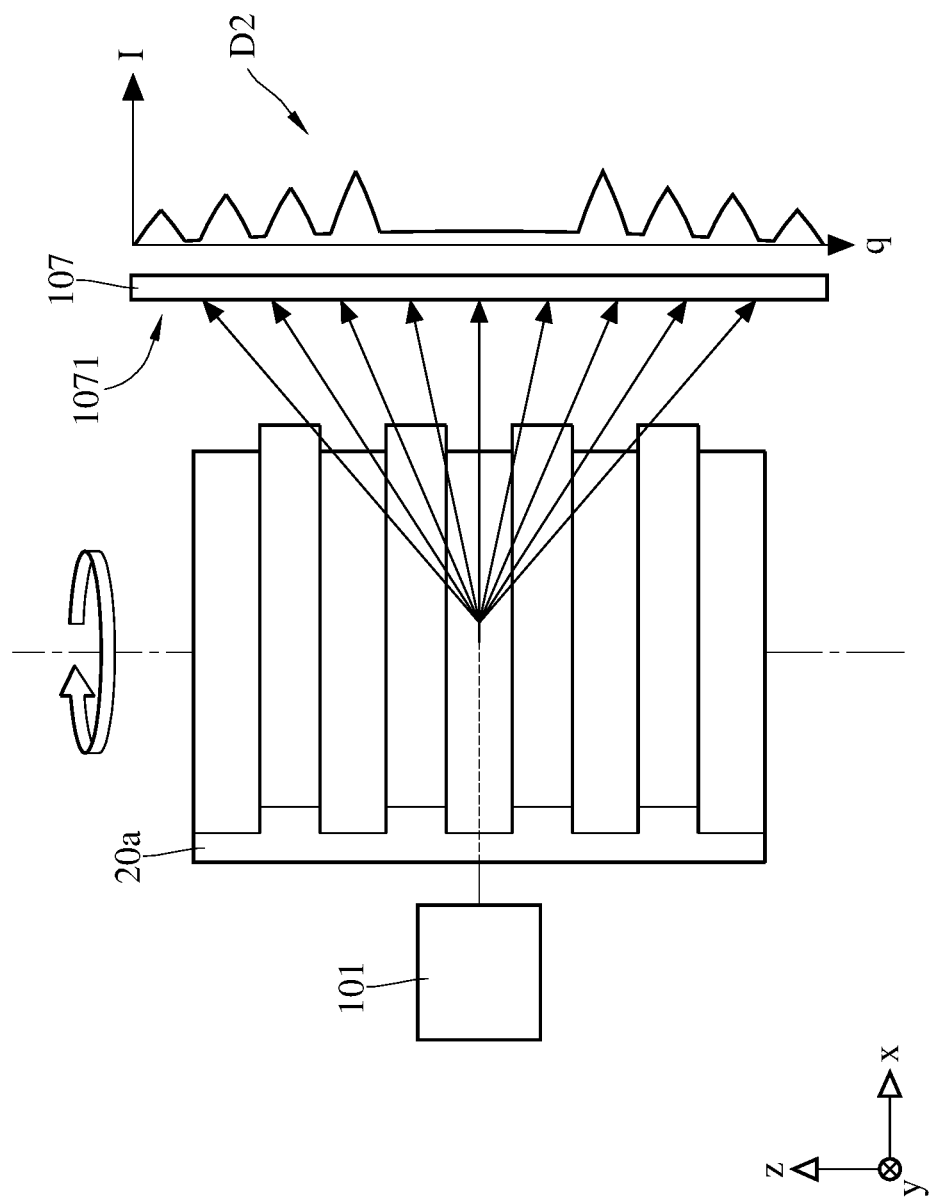
FIG. 4B is a schematic view showing an intensity distribution for that the first test piece is not orthogonal to X axis according to another embodiment of this disclosure.
Figure 4C:
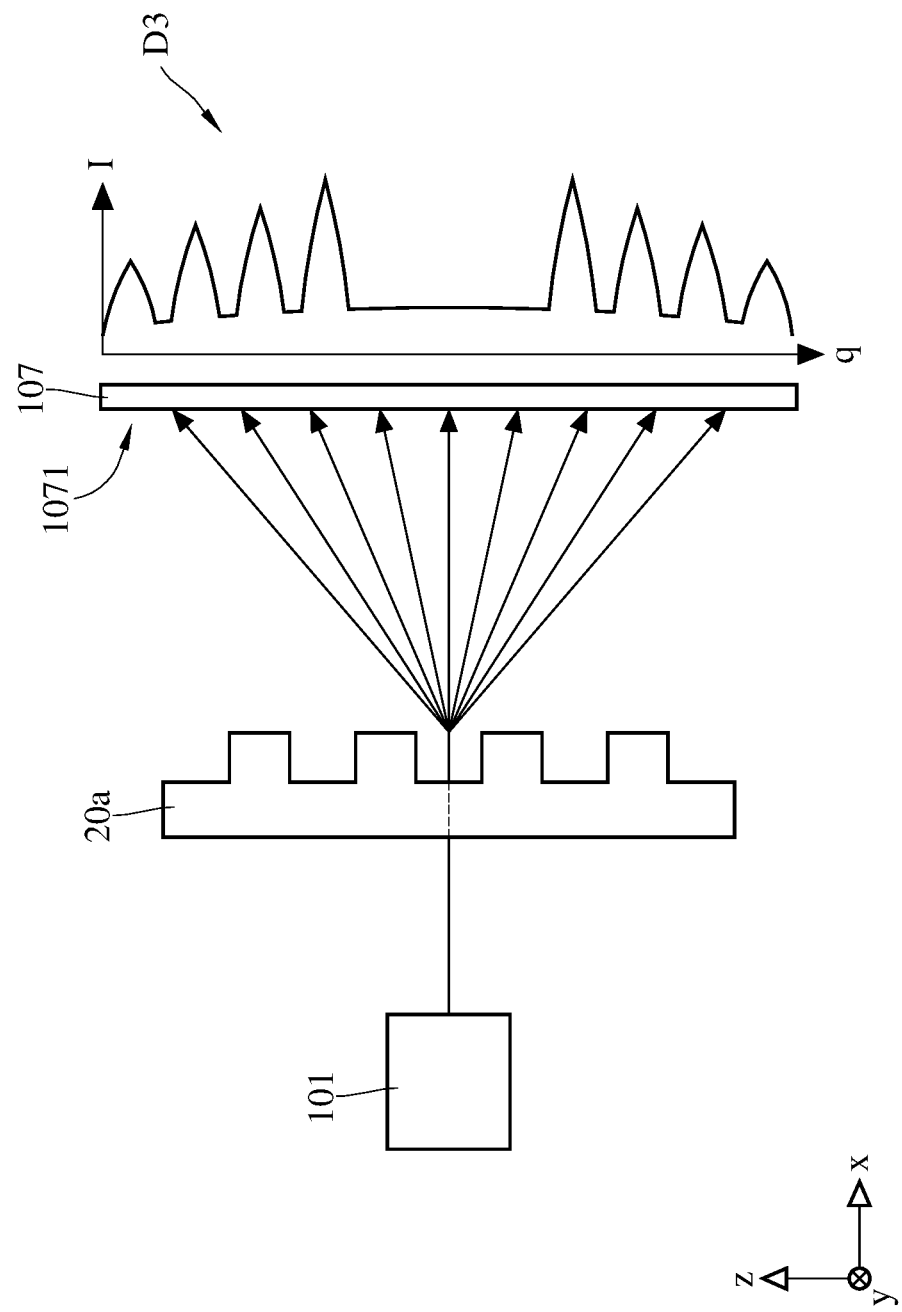
FIG. 4C is a schematic view showing an intensity distribution for that the first test piece is orthogonal to X axis according to another embodiment of this disclosure.

Referring to FIG. 4A, FIG. 4B and FIG. 4C, wherein FIG. 4A is a schematic view showing an intensity distribution for that the first test piece is not orthogonal to X axis according to an embodiment of this disclosure, FIG. 4B is a schematic view showing an intensity distribution for that the first test piece is not orthogonal to X axis according to another embodiment of this disclosure, and FIG. 4C is a schematic view showing an intensity distribution for that the first test piece is orthogonal to X axis according to another embodiment of this disclosure. In order to indicate that the scattering pattern is affected by different positions, FIG. 4A, FIG. 4B and FIG. 4C merely show the light source 101, the first test piece 20a, the sensing module 107 and the intensity distribution of the scattering pattern obtained by the sensing module 107. In FIG. 4A, the first test piece 20a is orthogonal to the XZ plane, but the first test piece 20a is not orthogonal to the light incident axis (that is, the X axis). In FIG. 4B, the first test piece 20a is orthogonal to the XY plane, but the first test piece 20a is not orthogonal to the light incident axis. In FIG. 4C, the first test piece 20a is orthogonal to the light incident axis.

As shown in FIG. 4A, there is an included angle θ1 between the first test piece 20a and X axis. At this time, the sensing module 107 obtains the intensity distribution D1, correspondingly. Similarly, in the embodiment that FIG. 4B corresponds to, the first test piece 20a is not orthogonal to X axis. At this time, the sensing module 107 obtains the intensity distribution D2, correspondingly. In the embodiment that FIG. 4C corresponds to, the first test piece 20a is orthogonal to X axis. At this time, the sensing module 107 obtains the intensity distribution D3, correspondingly.

Figure 4D:
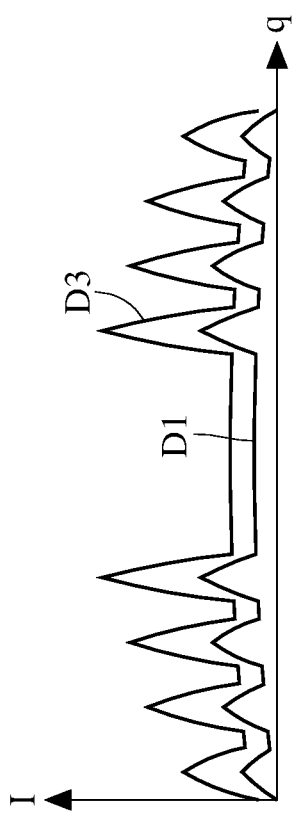
FIG. 4D is a schematic view illustrating the superposition of the intensity distribution in FIG. 4A.
Figure 4E:
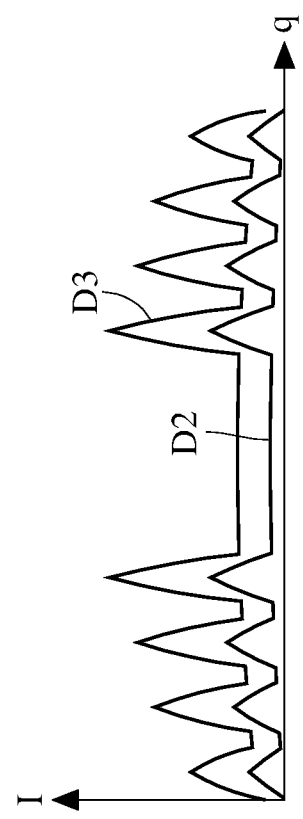
FIG. 4E is a schematic view illustrating the superposition of the intensity distribution in FIG. 4B.

FIG. 4D and FIG. 4E explain the relationship between the intensity distributions D1, D2 and D3. FIG. 4D is a schematic view illustrating the superposition of the intensity distribution in FIG. 4A and the intensity distribution in FIG. 4C. FIG. 4E is a schematic view illustrating the superposition of the intensity distribution in FIG. 4B and the intensity distribution in FIG. 4C. As shown in FIG. 4D and FIG. 4E, the scattering intensity of at least one partial area of the intensity distribution D3 is greater than the scattering intensity of the corresponding area of the intensity distribution D1. The scattering intensity of at least one partial area of the intensity distribution D3 is greater than the scattering intensity of the corresponding area of the intensity distribution D2. In other words, when the first test piece 20a is orthogonal to the light incident axis (that is, the X axis), the intensity of the scattering pattern generated by the X ray passing through the first test piece will be greater. On the contrary, by checking that if the intensities of one or more partial areas are greater than corresponding threshold values, the range of an included angle between the first test piece 20a and X axis or that if the first test piece 20a is orthogonal to the X axis may be determined.

As mentioned above, the controlling module 111 is used to obtain scattering light intensities corresponding to the scattering pattern and to drive the first multi-axis moving platform 103 pivoting the first test piece 20a along a first axis or a second axis according to the scattering light intensities until the scattering light intensities are greater than a predetermined value. In practice, the initial position of the first test piece 20a may be close to the position which is substantially orthogonal to X axis. Therefore, in an embodiment, the controlling module 111 drives the first multi-axis moving platform 103 to pivot the first test piece 20a with several possible angles and to make the first test piece 20a orthogonal to the X axis according to the scattering intensity.

The controlling module 111 is also used to drive the second multi-axis moving platform 105 to pivot the second test piece 20b along a third axis or a fourth axis according to the measurement distances d1', d2', d3' until the difference values of any two of the measurement distances d1', d2', d3' are less than a predetermined threshold value. The third axis is different from a fourth axis. The third axis, the fourth axis and the light incident axis are non-coplanar. In order to explain clearly, the third axis is defined as the Y axis while the fourth axis is defined as the Z axis.

The controlling module 111 is further used to move the first test piece 20a or the second test piece 20b until a test distance between the first test piece 20a and the second test piece 20b is less than the aforementioned interference distance. In an embodiment, the controlling module 111 moves the first test piece 20a or the second test piece 20b according to the measurement distances d1, d2, d3 until a test distance between the first test piece 20a and the second test piece 20b is less than the interference distance. In another embodiment, the controlling module 111 moves the first test piece 20a or the second test piece 20b according to a predetermined moving procedure until a test distance between the first test piece 20a and the second test piece 20b is less than the interference distance. To be more clearly, the first multi-axis moving platform 103 defines a first reference plane while the second multi-axis moving platform 105 defines a second reference plane. At least one partial area of the first reference plane is used as a reference position for the first test piece 20a while at least one partial area of the second reference plane is used as a reference position for the second test piece 20b. The first test piece 20a is disposed on or parallel to the first reference plane while the second test piece 20b is disposed on or parallel to the second reference plane. The controlling module 111 further determines a measurement distance between the first reference plane and the second reference plane according to the measurement distances d1', d2' and d3'. The controlling module 111 further drives the first multi-axis moving platform 103 to move the first reference plane along the light incident axis or drives the second multi-axis moving platform 105 to move the second reference plane along the light incident axis until the measurement distance is less than the interference distance.

In an embodiment, the controlling module 111 drives the first multi-axis moving platform 103 and the second multi-axis moving platform 105 to make the first test piece 20a orthogonal to the light incident axis and the second test piece 20b parallel to the second test piece 20b. The controlling module 111 then moves the first test piece 20a or the second test piece 20b until a measurement distance between the first test piece 20a and the second test piece 20b is less than the interference distance. By doing so, the damage of the test piece may be avoided, wherein this damage is caused by pivoting the first test piece 20a and the second test piece 20b to be orthogonal to the light incident axis after adjusting a relative distance between the first test piece 20a and the second test piece 20b. The measurement distance is, for example, a distance between the top of the periodic structure of the first test piece 20a and the top of the periodic structure of the second test piece 20b. When the measurement distance between the first test piece 20a and the second test piece 20b is less than the interference distance, an enhancing piece may be used to increase the intensity of the scattering pattern. Also, the enhancing piece, the interference component which is generated by the X ray passing through the test piece and the enhancing piece will increase the intensity of at least one part of the scattering pattern. A person having ordinary skill in the art may define the measurement distance and the interference distance according to practical needs.

Figure 5A:
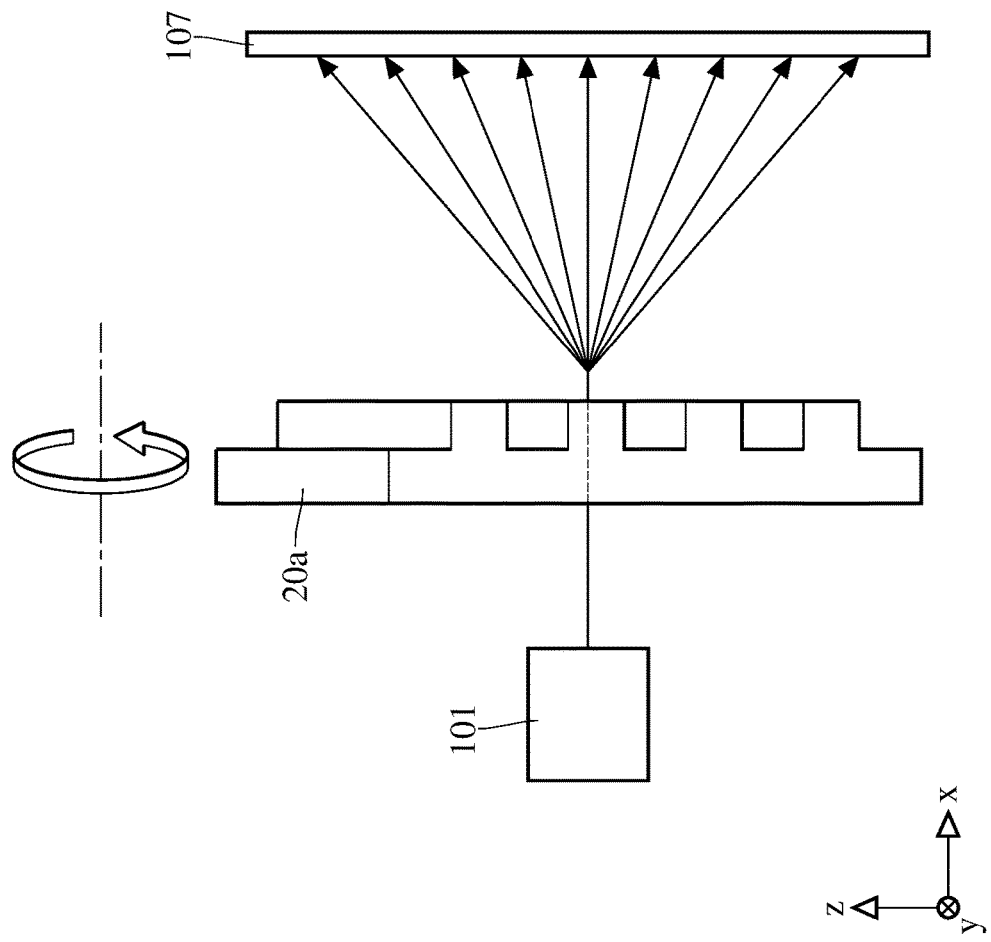
FIG. 5A is a schematic view illustrating a first test piece which is orthogonal to X axis but not disposed at a testing position according to another embodiment.
Figure 5C:
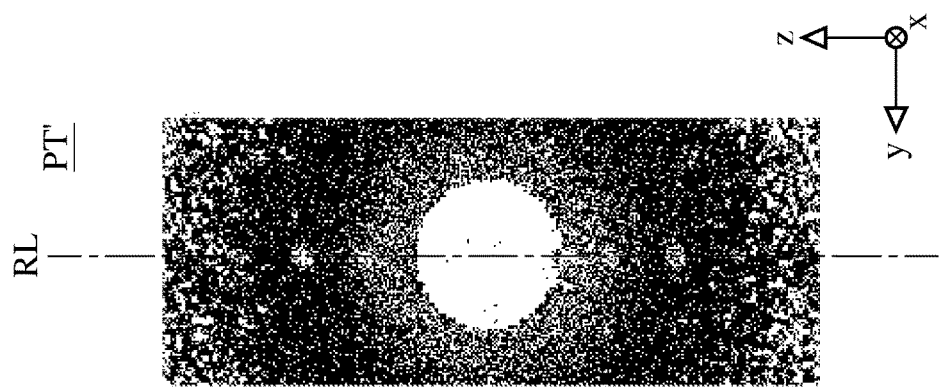
FIG. 5C shows a corresponding scattering pattern for the scenario that a first test piece orthogonal to X axis and disposed at a testing position according to another embodiment.
Figure 5B:
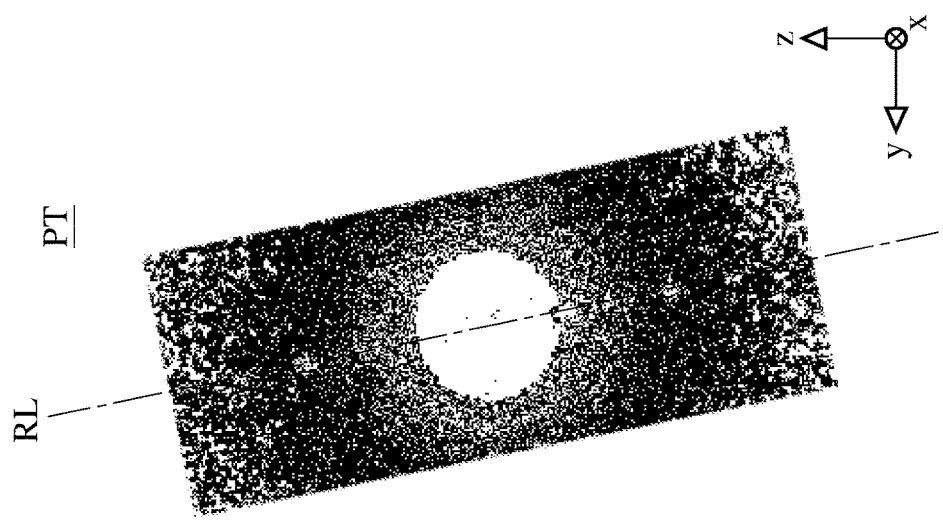
FIG. 5B is a corresponding scattering pattern according to FIG. 4A.

Referring to FIG. 5A, FIG. 5B and FIG. 5C, wherein FIG. 5A is a schematic view illustrating a first test piece which is orthogonal to X axis but not disposed at a testing position according to another embodiment, FIG. 5B is a corresponding scattering pattern according to FIG. 4A, and FIG. 5C shows a corresponding scattering pattern for a first test piece orthogonal to X axis and disposed at a testing position according to another embodiment. As shown in FIG. 5A, the first test piece 20a is orthogonal to the light incident axis (that is, the X axis), but the first test piece 20a is not parallel to the Y axis or the Z axis. Correspondingly, as shown in FIG. 5B, while the X ray passes through the first test piece 20a shown in FIG. 5A, the reference axial direction RL of the scattering pattern formed by the X ray is not parallel to the Z axis. In an embodiment, the aforementioned testing position is, for example, the position where the reference axial direction RL is parallel to the Z axis. Therefore, as shown in FIG. 5C, the controlling module 111 drives the first multi-axis moving platform 103 to pivot the first test piece 20a along the X axis to make the reference axial direction RL of the first test piece 20a parallel to the Z axis and the first test piece 20a disposed at a predetermined testing position.

Similarly, the controlling module 111 drives the second multi-axis moving platform 105 which pivots the second test piece along the X axis to make the position of the second test piece match the position of the first test piece. In an embodiment, the controlling module 111 drives the first multi-axis moving platform 103 which pivots the first test piece to be orthogonal to the light incident axis and located at the testing position. The controlling module 111 then drives the second multi-axis moving platform 105 which adjusts the second test piece to make the second test piece parallel to the first test piece. The controlling module 111 also drives the second multi-axis moving platform 105 to pivots the second test piece along the X axis, and checks that if the position of the second test piece matches the position of the first test piece according to the intensity of the scattering pattern obtained by the sensing module 107. Theoretically, when the position of the second test piece matches the position of the first test piece, the intensity of the scattering pattern will be higher. Therefore, in practice, if the intensity of the scattering pattern is greater than a threshold value, the controlling module 111 determines that the position of the second test piece matches the position of the first test piece.

In another embodiment, the shift measuring sensors 109a, 109b and 109c take measurements in an optical way. For example, there are several reflective coated areas on the first test piece. The relative locations of these reflective coated areas correspond to the relative locations of the shift measuring sensors 109a, 109b and 109c. In other words, when the reflective coated areas on the first test piece respectively align with the shift measuring sensors 109a, 109b and 109c, the measurement signals received by the shift measuring sensors 109a, 109b and 109c will be higher. That is, in this embodiment, when the measurement signals received by the shift measuring sensors 109a, 109b and 109c are greater than corresponding threshold values, the controlling module 111 determines that the position of the second test piece matches the position of the first test piece.

Figure 6:
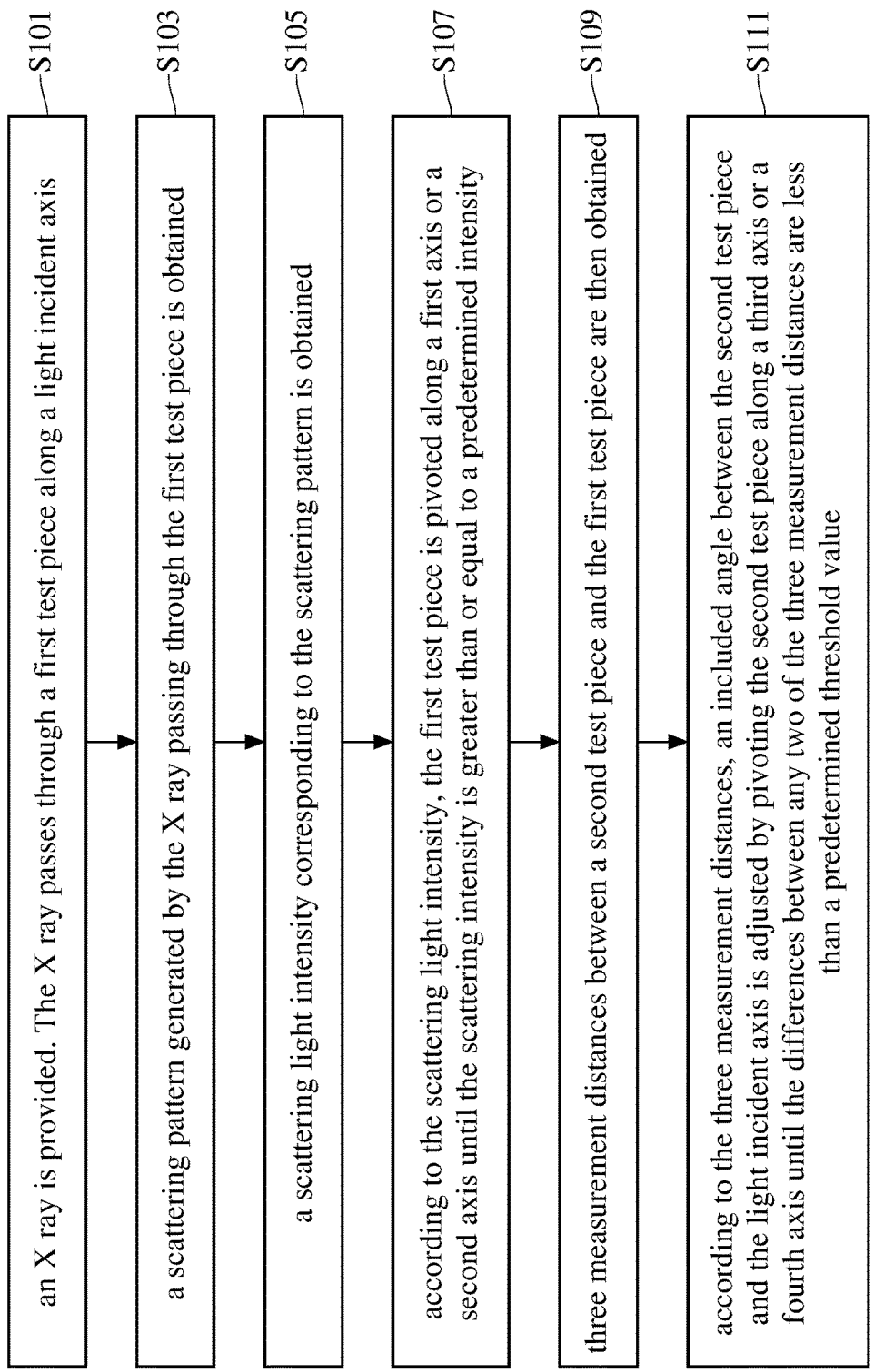
FIG. 6 shows a flowchart of a contactless dual-plane positioning method according to an embodiment of this disclosure.

FIG. 6 shows a flowchart of a contactless dual-plane positioning method according to an embodiment of this disclosure. Referring to FIG. 6. In step S101, an X ray is provided, wherein the X ray passes through a first test piece along a light incident axis. In step S103, a scattering pattern generated by the X ray passing through the first test piece is obtained. In step S105, a scattering light intensity corresponding to the scattering pattern is obtained. In step S107, according to the scattering light intensity, the first test piece is pivoted along a first axis or a second axis until the scattering intensity is greater than or equal to a predetermined intensity. In step S109, at least three measurement distances between a second test piece and the first test piece are then obtained, wherein the light incident axis passes through the plane defined by measurement points that the three measurement distances correspond to. In step S111, according to the three measurement distances, an included angle between the second test piece and the light incident axis is adjusted by pivoting the second test piece along a third axis or a fourth axis until the differences between any two of the three measurement distances are less than a predetermined threshold value. The third axis is different from a fourth axis. The third axis, the fourth axis and the light incident axis are non-coplanar.

In summary, this disclosure discloses a contactless dual-plane positioning method and a contactless dual-plane positioning device. According to the contactless dual-plane positioning method, the position of the first test piece is adjusted to make the first test piece orthogonal to the light incident according to the scattering light intensity corresponding to the scattering pattern. The position of the second test piece is adjusted to make the second test piece parallel to the first test piece (equivalent to that the second test piece is orthogonal to the light incident axis) by adjusting the position of the second test piece according to several measurement distances between the first test piece and the second test piece. The measurement distances between the first test piece and the second test piece are then adjusted to make that a test distance between the first test piece and the second test piece is less than an interference distance. By using the contactless dual-plane positioning method and the dual-plane positioning device, the first test piece and the second test piece are parallel to each other and orthogonal to the light incident axis. The first test piece and the second test piece are disposed, with the test distance being less than the interference distance, so as to achieve a better effect of enhancing the X ray. In addition, the first test piece or the second test piece is not limited to an enhancing piece or a test piece. The flexibility of the relative procedures may be increased.

It will be apparent to those skilled in the art that various modifications and variations can be made to the structure of the disclosed embodiments. It is intended that the specification and examples be considered as exemplars only, with a true scape of the disclosure being indicated by the following claims and their equivalents.

What is claimed is:

1. A contactless dual-plane positioning method, comprising:
providing an X ray, wherein the X ray passes through a first test piece along a light incident axis;
obtaining a scattering pattern generated by the X ray passing through the first test piece;
obtaining a scatting light intensity corresponding to the scattering pattern;
pivoting the first test piece along a first axis or a second axis according to the scattering light intensity until the scattering intensity is greater than or equal to a predetermined intensity, wherein the first axis is different from the second axis and the first axis while the second axis and the light incident axis are non-coplanar;
obtaining three measurement distances between a second test piece and the first test piece, wherein the incident light axis passes through a plane defined by at least three corresponding measurement points of the three measurement distances; and
adjusting an included angle between the second test piece and the light incident axis by pivoting or moving the second test piece along a third axis or a fourth axis according to the three measurement distances until the differences between any two of the three measurement distances are less than a predetermined threshold value.

2. The contactless dual-plane positioning method according to claim 1, further comprising:
moving the first test piece or the second test piece along the light incident axis according to the three measurement distances until a test distance between the first test piece and the second test piece is less than an interference distance.

3. The contactless dual-plane position method according to claim 2, wherein the interference distance is not greater than 500 nm.

4. The contactless dual-plane positioning method according to claim 1, further comprising pivoting the first test piece or the second test piece along the light incident axis according to intensities of measurement signals of a plurality of shift measurement detectors until the scattering pattern is rotated to a measurement position.

5. The contactless dual-plane positioning method according to claim 1, further comprising:
obtaining an enhancement scattering pattern generated by the X ray passing through the first test piece and the second test piece;
obtaining an enhancement scattering light intensity according to the enhancement scattering pattern; and
pivoting the first test piece or the second test piece along the light incident axis according the enhancement scattering light intensity until the enhancement scattering light intensity is greater than another predetermined intensity.

6. The contactless dual-plane positioning method according to claim 1, wherein the third axis is different from the fourth axis while the third axis, the fourth axis and the light incident axis are non-coplanar.

7. A contactless dual-plane positioning device, comprising:
a light source having a light emitting end, wherein the light source provides an X ray through the light emitting end, wherein the X ray propagates along a light incident axis;
a first multi-axis moving platform, moving or pivoting a first test piece along multiple axes;
a second multi-axis moving platform, moving or pivoting a second test piece along the multiple axes;
a sensing module having a light sensing plane, wherein the light sensing plane faces the light emitting end, wherein the first multi-axis moving platform and the second multi-axis moving platform are disposed between the light emitting end and the light sensing plane, wherein the sensing module obtains a scatting pattern generated by the X ray passing through the first test piece;
three shift measuring detectors obtain a plurality measurement results related to at least three measurement distances between the first test piece and the second test piece,
wherein the three shift measuring detectors are not collinear while the light incident axis passes through a plane defined by the three shift measuring detectors; and
a controlling module electrically connected to the sensing module, the first multi-axis moving platform, the second multi-axis moving platform, and the three shift measuring detectors, wherein the controlling module obtains a scatting light intensity corresponding to the scatting pattern and drives the first multi-axis moving platform which pivots the first test piece along a first axis or a second axis according to scattering light intensity until the scatting light intensity is greater than a predetermined intensity, wherein the controlling module drives the second multi-axis moving platform which pivots the second test piece along a third axis or a fourth axis according to the three measurement distances until differences of any two of the three measurement distances are less than a predetermined threshold value, and wherein the first axis is different from the second axis while the first axis, the second axis and the light incident axis are non-coplanar.

8. The contactless dual-plane positioning device according to claim 7, wherein the first multi-axis moving platform defines a first reference plane while the second multi-axis moving platform defines a second reference plane, wherein the first test piece is disposed on the first reference plane while the second test piece is disposed on the second reference plane, wherein the controlling module determines a test distance between the first reference plane and the second reference plane according the three measurement distances, and wherein the controlling module drives the first multi-axis moving platform which moves the first reference plane along the light incident axis or drives the second multi-axis moving platform which moves the second reference plane along the light incident axis until the test distance is less than an interference distance.

9. The contactless dual plane position device according to claim 8, wherein the interference distance is not greater than 500 nm.

10. The contactless dual-plane positioning device according to claim 7, wherein the controlling module further drives the first multi-axis moving platform which pivots the first test piece along the light incident axis or drives the second multi-axis moving platform which pivots the second test piece along the light incident axis according to intensities of measurement signals of the three shift measuring detectors until the scatting pattern is rotated to a measurement position.

11. The contactless dual-plane positioning device according to claim 7, wherein the sensing module further obtains an enhancement scattering pattern generated by the X ray passing through the first test piece and the second test piece, wherein the controlling module further obtains an enhancement scattering light intensity according to the enhancement scattering pattern, and wherein the controlling module drives the first multi-axis moving platform which pivots the first test piece along the light incident axis or drives the second multi-axis moving platform which pivots the second test piece along the light incident axis according the enhancement scattering light intensity until the enhancement scattering light intensity is greater than another predetermined intensity.

12. The contactless dual-plane positioning device according to claim 7, wherein the third axis is different from the fourth axis while the third axis, the fourth axis and the light incident axis are non-coplanar.

\* \* \* \* \*